2/21/84 OR 4,432,371

United States Patent [19]

McAusland

[11] 4,432,371

[45] Feb. 21, 1984

[54] ULTRASOUND SCANHEAD

[75] Inventor: Robert R. McAusland, Seattle, Wash.

[73] Assignee: Advanced Technology Laboratories, Inc., Bellevue, Wash.

[21] Appl. No.: 386,869

[22] Filed: Jun. 10, 1982

[51] Int. Cl.³ .............................................. A61B 10/00
[52] U.S. Cl. ...................................................... 128/660
[58] Field of Search .................... 128/660, 661; 73/644

[56] References Cited

U.S. PATENT DOCUMENTS 4,185,501 1/1980 Proudian et al. ............... 128/660 X
4,316,271 2/1982 Evert .............................. 128/660 X

*Primary Examiner*—Kyle L. Howell
*Assistant Examiner*—Francis J. Jaworski
*Attorney, Agent, or Firm*—Lawrence S. Levinson; Sanford J. Asman

[57] ABSTRACT

The scanhead includes an impeller which is designed to swirl the liquid adjacent the ultrasound transducers as the transducers are rotated. The fluid dynamics established by the swirling liquid cause any bubbles within the liquid to be forced to the center of the swirling liquid where they are out of the zone of transmitted or received ultrasound energy. When an impeller having multiple vanes with an opening formed therebetween is used, the bubbles are forced to the center of the impeller.

1 Claim, 3 Drawing Figures

ULTRASOUND SCANHEAD

BACKGROUND OF THE INVENTION

The present invention relates to an improved ultrasound scanhead of the type used for medical diagnosis.

Mechanical ultrasound scanheads of the type which employ a number of piezoelectric transducers to generate and receive ultrasound energy are known. A typical scanhead includes at least one piezoelectric transducer mounted on a rotating armature and arranged electrically so that only one transducer is active at any time. In a typical mechanical ultrasound scanhead, the transducers are mounted in a viscous fluid capable of efficiently transferring ultrasound energy. Typically, mineral oil is used for this purpose.

Heretofore, air bubbles in the mineral oil have caused problems with the ultrasound imaging as they interfere with ultrasound transmission and reception. The typical approach heretofore used to avoid problems caused by bubbles has been to attempt to remove the air bubbles from the mineral oil. Unfortunately, the viscosity of the mineral oil and the fact that the bubbles tend to stick to the walls of the transducer and to the interior walls and elements of the scanhead makes it particularly difficult to remove all of the bubbles.

SUMMARY OF THE INVENTION

In accordance with the present invention, an impeller, preferably having a central opening, is preferably provided at the end of the armature on which the ultrasound transducers are mounted. Accordingly, when the armature rotates, the spinning impeller, in combination with the viscosity of the mineral oil, forces any bubbles into the central opening between the impeller vanes. Thus, despite the fact that air bubbles may remain in the mineral oil, they are forced into a position where they are out of the zone of ultrasound transmission and reception.

DETAILED DESCRIPTION OF THE PREFERRED EMBODIMENT

Figures 1, 2, 3:
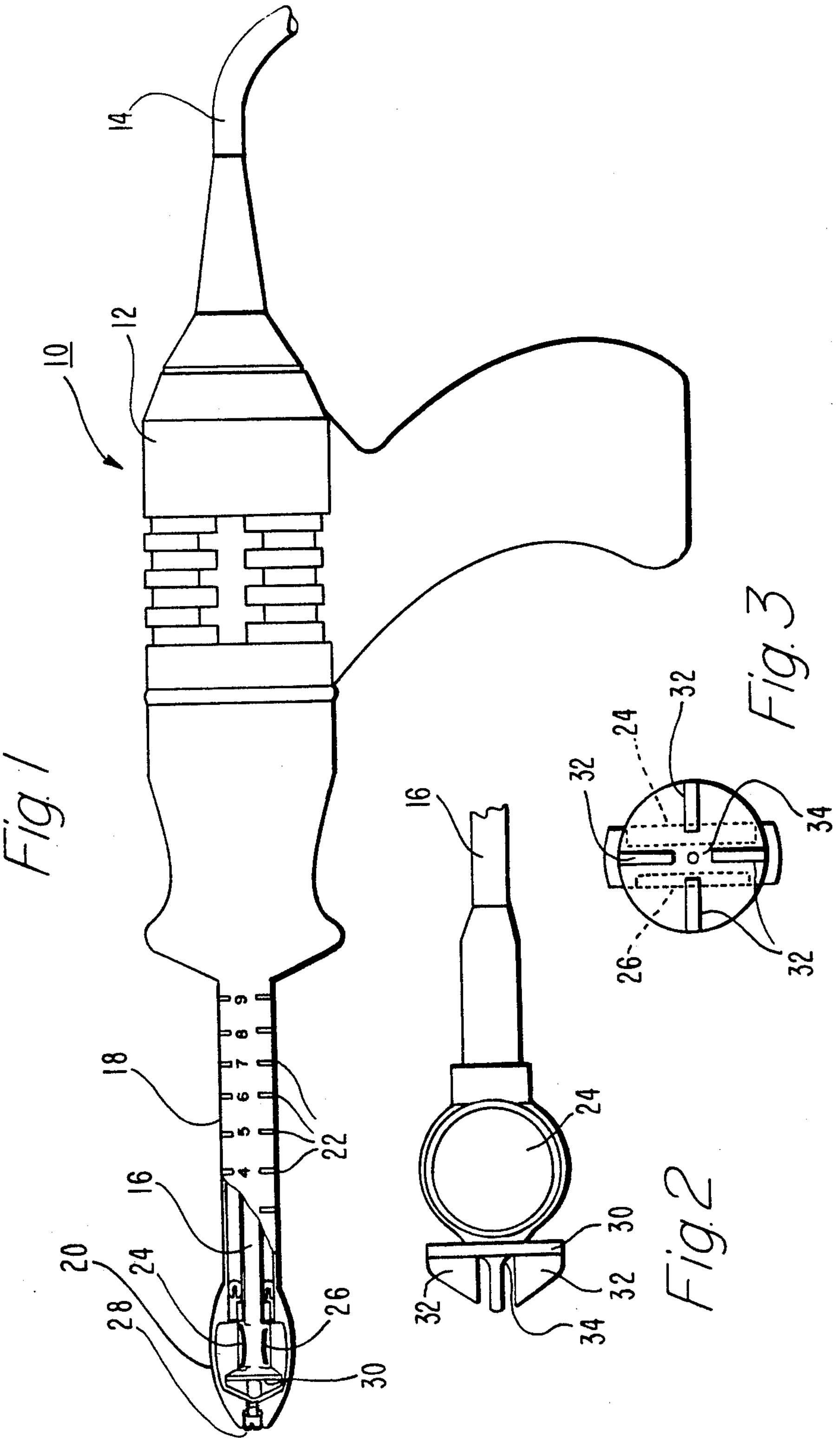
FIG. 1 is a side view of a prostate scanhead which employs the present invention.
FIG. 2 is a side view of the end portion of the armature of the ultrasound scanhead of FIG. 1.
FIG. 3 is an end view illustrating the impeller on the end of the armature adjacent to the ultrasound transducers.

Referring now to FIG. 1, a mechanical prostate scanhead 10, which employs the present invention, is shown. The scanhead 10 includes a motor housing 12 which contains a motor, motor controller electronics, reed switches, transformer, and other items typically found in a conventional mechanical, ultrasound sector scanner. The scanhead 10 is connected to the electronic apparatus used to generate the ultrasound energy and to display the resulting video images via a cable 14.

An armature 16 extends through a tubular extension 18 from the motor (not shown) in the motor housing 12 to a transducer housing 22 at the end of the tubular extension 18. In the prostate scanhead 10 of the preferred embodiment, the outside of the tubular extension 18 is marked with indicia 20 to indicate the depth of insertion of the device 10 when it is in use.

In the preferred embodiment of the invention, two piezoelectric transducers 24, 26 which operate in the 5.0 MHz and 7.5 MHz frequency regions, respectively, are mounted on the armature 16. When the scanhead 10 is in use, the transducers 24, 26 rotate within the transducer housing 22.

A fill port 28 is located at the extreme end of the transducer housing 22. The fill port 28 is used to fill the transducer housing 22 with mineral oil.

In accordance with the present invention, an impeller 30 is mounted within the transducer housing 20 on the extreme end of the armature 16. In the preferred embodiment of the invention, the impeller 30, shown in FIGS. 1-3, comprises four vanes 32, and it preferably has a central opening 34 formed between the vanes 32, as shown in FIGS. 1-3.

In the operation of the scanhead 10, as the armature 16 rotates each of the transducers 24, 26 passes through a particular sector, typically a 90 degree scan sector, a conventional magnetic reed switch (not shown) mounted within the motor housing 12 is closed, thereby energizing the associated transducer 24, 26 through an armature-mounted transformer (also within the housing 12), in a manner well known in the art.

Any bubbles which are present in the mineral oil in the area of the transducers 24, 26 are forced, by the density gradient created by the centrifugal field created by the impeller 30, into the central opening 34 where they are out of the zone of ultrasound energy produced or detected by the transducers 24, 26. Consequently, the use of the present invention removes the problems heretofore caused by bubbles which interfere with the transmission or reception of ultrasound energy.

While the precise mechanism for the removal of the bubbles from the region of the transducers is not well known, it is hypothesized that the bubbles, being less dense than the mineral oil, are drawn to the center of the density gradient created by the centrifugal field created by the impeller, as the more dense mineral oil is thrown outward by centrifugal force. Accordingly, as will be understood by those skilled in the art, while the preferred embodiment of the invention, as described herein, employs a vane-type impeller mounted on the end of the armature, other embodiments of the invention could use other types of impellers, with or without vanes, for the same purpose without departing from the spirit or scope of the present invention. Similarly, while it is preferable to use a central opening between the impeller vanes, an impeller with no central opening could also be used to trap the bubbles.

I claim:

1. An improved ultrasound scanhead of the type comprising a housing containing a motor: an armature extending from the motor: at least one ultrasound transducer mounted in a liquid containing transducer housing adjacent one end of the armature, wherein the improvement comprises an impeller comprising a substantially circular disk mounted on the end of said armature, said impeller including a plurality of vanes which extend outward from said disk for causing said liquid to rotate, there being a central opening between said vanes into which any bubbles contained within said liquid will be forced when said impeller rotates, said central opening not being within the zone of transmitted or received ultrasound energy.

* * * * *